United States Patent
Ye et al.

(10) Patent No.: US 9,671,317 B2
(45) Date of Patent: *Jun. 6, 2017

(54) AUTOMATIC INJECTION DEVICE FOR MICROARRAY CHIP AND AUTOMATIC INJECTION HYBRIDIZATION MICROARRAY CHIP

(75) Inventors: Jiaming Ye, Beijing (CN); Pinhong Wang, Beijing (CN); Guoqing Wang, Beijing (CN); Wanli Xing, Beijing (CN)

(73) Assignees: CAPITALBIO CORPORATION, Beijing (CN); TSINGHUA UNIVERSITY, Beijing (CN)

( * ) Notice: Subject to any disclaimer, the term of this patent is extended or adjusted under 35 U.S.C. 154(b) by 811 days.

This patent is subject to a terminal disclaimer.

(21) Appl. No.: 14/006,488

(22) PCT Filed: Feb. 10, 2012

(86) PCT No.: PCT/CN2012/070999
§ 371 (c)(1),
(2), (4) Date: Sep. 20, 2013

(87) PCT Pub. No.: WO2012/126293
PCT Pub. Date: Sep. 27, 2012

(65) Prior Publication Data
US 2014/0011703 A1    Jan. 9, 2014

(30) Foreign Application Priority Data
Mar. 22, 2011   (CN) .......................... 2011 1 0068676

(51) Int. Cl.
*G01N 1/10*    (2006.01)
*G01N 35/10*    (2006.01)
(Continued)

(52) U.S. Cl.
CPC ............. *G01N 1/10* (2013.01); *C12Q 1/6813* (2013.01); *G01N 35/1095* (2013.01);
(Continued)

(58) Field of Classification Search
None
See application file for complete search history.

(56) References Cited

U.S. PATENT DOCUMENTS

2003/0157503 A1*   8/2003   McGarry et al. . B01L 3/502715
435/6.11

FOREIGN PATENT DOCUMENTS

CN        101221168        7/2008
CN        201331523        10/2009
(Continued)

OTHER PUBLICATIONS

Pantoja et al., "Silicon chip-based patch-clamp electrodes integrated with PDMS microfluidics," Biosens. Bioelectron. 2004, 20:509-517.*

(Continued)

*Primary Examiner* — Kaijiang Zhang
(74) *Attorney, Agent, or Firm* — Merchant & Gould P.C.

(57) ABSTRACT

An automatic injection device comprises at least an injection unit (1). The said injection unit (1) is formed by sealing a cover plate layer (3) with hydrophilic surfaces and a microfluid layer (4). The said cover plate layer (3) is provided with at least two through holes (5). The said microfluid layer (4) is provided with a hollow-out hybridization chamber (7) and at least two hollow-out microfluid channels (6). One end of each channel (6) is connected with the hybridization chamber (7), and the other end is connected with a through hole (5) of the cover plate layer (3) respectively. Taking advantage of the hydrophilicity of the cover plate, the automatic injection device makes a solution automatically enter and fill (Continued)

the hybridization chamber (7) and the microfluid channels (6) by the driving force of liquid surface tension. The flow uniformity of sample solution in microarray chip is achieved by the structural design of the hybridization chamber (7) and the microfluid channels (6). The automatic injection device has advantages of simple manufacture, easy operation, high hybridization efficiency, low sample cost, and automatic quantificational injection.

14 Claims, 4 Drawing Sheets

(51) Int. Cl.
| | |
|---|---|
| *C12Q 1/68* | (2006.01) |
| *G01N 33/543* | (2006.01) |
| *G01N 33/68* | (2006.01) |
| *C40B 30/04* | (2006.01) |
| *C40B 40/06* | (2006.01) |
| *C40B 40/10* | (2006.01) |
| *C40B 40/12* | (2006.01) |

(52) U.S. Cl.
CPC .............. *C40B 30/04* (2013.01); *C40B 40/06* (2013.01); *C40B 40/10* (2013.01); *C40B 40/12* (2013.01); *G01N 33/543* (2013.01); *G01N 33/68* (2013.01)

(56) References Cited

FOREIGN PATENT DOCUMENTS

| | | |
|---|---|---|
| CN | 102199529 | 9/2011 |
| CN | 102206573 | 10/2011 |
| CN | 102250751 | 11/2011 |
| WO | WO 2009/136892 | 11/2009 |

OTHER PUBLICATIONS

International Search Report from International Application No. PCT/CN2012/070999 mailed May 17, 2012.

\* cited by examiner (a)

(b)

AUTOMATIC INJECTION DEVICE FOR MICROARRAY CHIP AND AUTOMATIC INJECTION HYBRIDIZATION MICROARRAY CHIP

The present application is a National Stage Application of PCT/CN2012/070999, filed Feb. 10, 2012, which claims benefit claims the priority of Chinese patent application No. 201110068676.0 filed on Mar. 22, 2011 in The Patent Office of the People's Republic of China, and titled "Automatic sample loading device for microarray chip and automatic sample loading hybridization microarray chip", which applications are incorporated herein by reference. To the extent appropriate, a claim of priority is made to each of the above disclosed applications.

FIELD OF INVENTION

The present invention relates to the field of biotechnology, in particular, to an automatic sample loading device for microarray chip and automatic sample loading hybridization microarray chip.

BACKGROUND OF THE INVENTION

Nucleic acid hybridization is based on the specific binding between complementary DNA chains, which are currently broadly used for gene expression analysis, gene phenotype analysis and clinical diagnosis etc. For conventional static nucleic acid hybridization represented by microarray chip, the hybridization process simply relies on molecular diffusion, that is, target molecules must diffuse from the solution to the substrate surface coated with probe, and then recognize and interact with the probe. However, the hybridization process may cost hours due to the extremely small diffusion coefficient of a target nucleic acid molecules. Additionally, the sample loading for such microarray chip is mainly realized by using delicate sampling device such as pipette, which greatly limits the use of microarray chip and needs highly qualified operators.

At present, a number of hybridization chips have been developed based on microfluidics to achieve shorter hybridization time and lower sample loss, which, depending on different mechanism, includes dynamic hybridization chip platforms based on electric force or magnetic stirring, mixing by vibration, continuous flow or circulation flow. However, due to the disadvantages such as complex chip preparation process, high sample loss, expensive external auxiliary apparatus, complicated operation process and incapability of multi-sample analysis, such techniques are still in research in laboratory, and can not be largely used or popularized.

SUMMARY

An objective of the present invention is to provide an automatic sample loading device, which allows the sample solution enter and fill the fluid chamber and channel automatically through liquid surface tension, in order to achieve the automatic quantificational sample loading.

The present application provides an automatic sample loading device, comprising at least one sample loading unit formed by sealing a cover layer with hydrophilic surface and a microfluid layer, wherein the cover layer is configured with at least two through holes, and the microfluid layer is configured with one hollow hybridization chamber and at least two hollow microfluid channels, wherein one end of each of said microfluid channel is connected to the hybridization chamber, and the other end is connected to one of the through hole in the cover layer.

Preferably, among the multiple microfluid channels, one of them can be used as fluid input channel, and a plurality of them can be used as the fluid output channel.

The cover layer with hydrophilic surface can be made from solid material with hydrophilic surface, or from common solid material which is modified to have hydrophilic surface. Said common solid material particularly includes glass, high molecular polymers, silicon wafer or metal and the oxides thereof.

Preferably, the contact angle between the surface of said cover layer with hydrophilic surface which contacts the microfluid layer and the hybridization sample solution can be in the range from 0 to 90 degree, more preferably, in the range from 0 to 15 degree, in order to ensure the effect of automatic sample loading; while the contact angle between the other surface and the hybridization sample solution can be in the range from 0 to 180 degree, more preferably, 90 to 180 degree, in order to ensure the effect of automatic sample loading.

The present application provides an automatic sample loading device, wherein the material for said cover layer is glass, high molecular polymers, silicon wafer, metals or metal oxides.

The present application provides an automatic sample loading device, wherein the sealing between the microfluid layer and the cover layer can be implemented by adhesion, welding or a sealing element. When the material for the microfluid layer is selected from glass, high molecular polymers, silicon wafer, metals or metal oxides, the sealing is preferably achieved by an adhesive; whereas the sealing also can be implemented by welding when the material for the microfluid layer is selected from metals or metal oxides.

Preferably, said microfluid layer is laminated by substrate layer, upper adhesive layer and lower adhesive layer. The material for the substrate layer is glass, high molecular polymers, silicon wafer, metal or metal oxides. The adhesive for both upper adhesive layer and lower adhesive layer is calendering adhesive, melt adhesive, reactive adhesive, solvent adhesive, emulsion adhesive or solventless liquid adhesive.

The present application provides an automatic sample loading device based on reciprocating flow, wherein the hybridization chamber and two microfluid channels of the microfluid layer have hollow structure, which can be formed by laser ablation, machining or chemical etching etc. The shape and area of the hybridization chamber correspond to those of the bio-probe array of the microarray chip, while the depth and length of the microfluid channel is determined by the amount of the sample solution.

The present invention further provides an automatic sample loading hybridization microarray chip, comprising the automatic sample loading device and the microarray chip, the microfluid layer of the automatic sample loading device is sealed with the microarray chip, while the hybridization chamber is connected with the bio-probe array of the microarray chip.

Preferably, said microarray chip is RNA chip, cDNA chip, PNA chip, protein chip or carbohydrate chip.

The present invention further provides the method for using the automatic sample loading device, comprising the following steps:

Step 1: the microfluid layer of the automatic sample loading device is sealed with the microarray chip, resulting in the connection between the hybridization chamber and the bio-probe array of the microarray chip;

Step 2: sample is loaded at one of the through holes of a sample loading unit of the automatic sample loading device, allowing the sample solution entering and filling the microfluid channel connected with said through hole;

Step 3: the through hole is connected to a pump valve which provides the gas pressure, allowing the sample solution to flow back and forth in the hybridization chamber and the two microfluid channels with the gas pressure as driving force.

The present invention provides an automatic sample loading device, wherein the position and shape of the hybridization chamber should ensure the homogeneity of the reaction between the sample solution and the bio-probe on the lower substrate; the microfluid channel is connected to the hybridization chamber, providing the space for the reciprocating flow of the sample solution; the hydrophilic property of the cover layer is utilized in the automatic sample loading device to allow the sample solution automatically entering and filling the hybridization chamber and flow channel with liquid surface tension as the driving force.

The present invention provides a method for using the automatic sample loading device, wherein the solution flows back and forth in the microfluid channel and the hybridization chamber with the gas pressure generated by syringe pump or plunger pump as the driving force; the reciprocating frequency of the reciprocating flow is preferably from 0 to 100 Hz, and the gas pressure providing the driving force for the reciprocating flow is preferably from 0 to 1 MPa.

The present invention provides a method for using the automatic sample loading device, further comprising the step of removing the sample solution from another through hole with the gas pressure as the driving force after the hybridization reaction is completed.

The list of the microarray chip is RNA chip, cDNA chip, PNA chip, protein chip or carbohydrate chip, and the bio-probes immobilized on the bio-probe array is be selected from one of the following biomolecule: RNA, cDNA, PNA, peptide, protein etc.

The advantages of the present invention are as follows: realization of automatic quantificational sample loading, improved hybridization efficiency, shorten the hybridization time to within 15 min, simple preparation, easy operation, low sample loss, capacity of automatic quantificational sample loading and thus worth of popularization.

DESCRIPTION OF THE PREFERRED EMBODIMENTS

An automatic sample loading device for microarray chip and the method for using said device are disclosed by the present invention, which can be implemented by properly modifying the processing parameters by the one of skill in the art with reference to the content herein. Particularly, it should be noted that all similar replacements and modifications are apparent to the one of skill in the art, all of which is regarded to be included in the present invention. The product of the present invention, as well as the method and the application thereof have been described by preferred Examples, and it is apparent that modification, or proper change and the combination thereof can be made to the method and the application described herein by those skilled in the art, without departing from the content, spirit and scope of the invention, in order to achieve and apply the techniques disclosed in the present invention.

The present invention will be further explained with reference to the specific Examples below, in order to make the technical proposal of the present invention better understood by one of ordinary skill in the art.

Example 1

Figure 1:
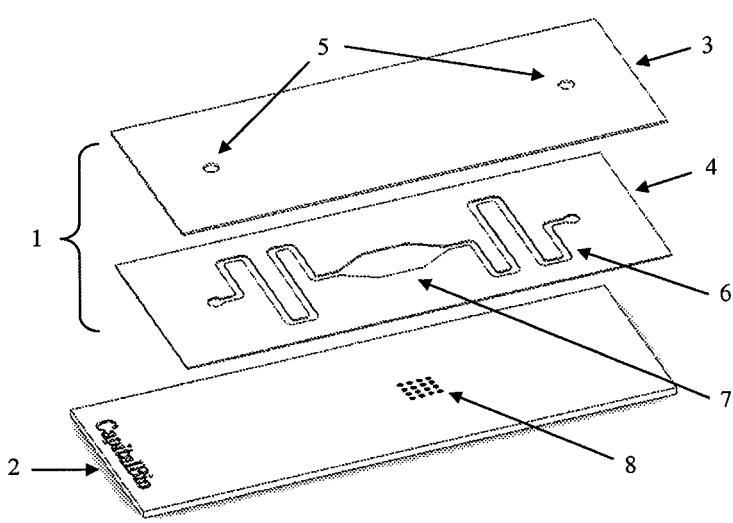
FIG. 1 is the schematic diagram showing the three-dimensional structure of the automatic sample loading device described in Example 1, wherein: 1 is the automatic sample loading device; 2 is the microarray chip; 3 is the cover plate; 4 is the microfluid layer; 5 is the through hole; 6 is the microfluid channel; 7 is the hybridization chamber; and 8 is the bio-probe array.
Figure 3:
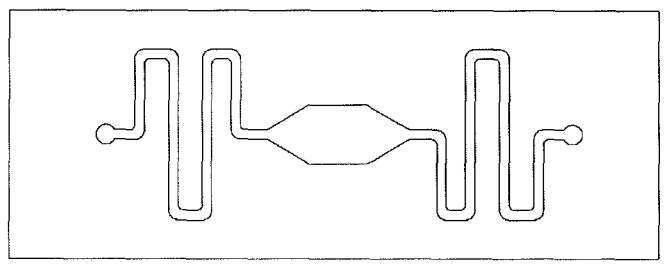
FIG. 3 is the schematic diagram showing the automatic sample loading device described herein; (a) the automatic sample loading device containing one sample loading unit; (b) the automatic sample loading device for the microarray hybridization platform containing four sample loading units.
Figure 3:
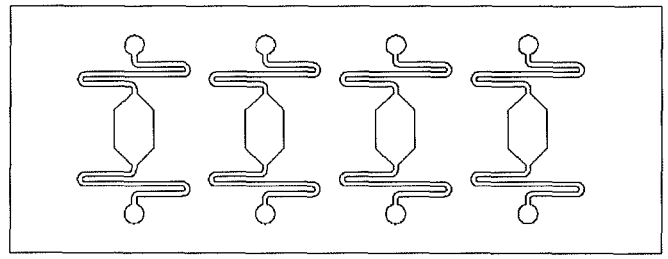

An Automatic Sample Loading Device and an Automatic Sample Loading Hybridization Microarray Chip Containing One Sample Loading Unit The three-dimensional structure of the automatic sample loading device containing one sample loading unit can be seen in FIG. 1, wherein 1 is the automatic sample loading device; 2 is the microarray chip, which is a glass based DNA chip or protein chip, with the size of 25×75 mm; 3 is the hydrophilic glass cover plate, after chemical modification, the lower surface of the glass cover plate, i.e., the surface contacting the microfluid layer 4, has a static contact angle of 12 degrees with water, while the upper surface has a static contact angle of 40 degrees with water; and through hole 5 is placed on the cover plate 3 for the solution to pass through; The thickness of the microfluid layer 4 is about 0.2 mm, the substrate of the microfluid layer is polyethylene terephthalate (PET), with both lower and upper surface homogenously coated by acrylic adhesive, and a hollow microfluid channel 6 and hybridization chamber 7 are disposed on the microfluid layer 4; the length of the single side of the microfluid channel 6 is 50 mm, with one end connected to the hybridization chamber 7, and the other end to the through hole 5 of the cover layer 3. An automatic sample loading device is formed by sealing the upper surface of the microfluid layer 4 and the lower surface of the cover plate 3 by acrylic adhesive. An automatic sample loading hybridization microarray chip is formed through sealing the lower surface of the microfluid layer 4 on said automatic sample loading device by the acrylic adhesive with the microarray chip 2, wherein the hybridization chamber 7 is connected to the bio-probe array 8 of the microarray chip, the shape and area of the hybridization chamber correspond to those of the bio-probe array of the microarray chip. FIG. 3(*a*) is the schematic diagram showing an automatic sample loading device containing one sample loading unit.

Example 2

Figure 2:
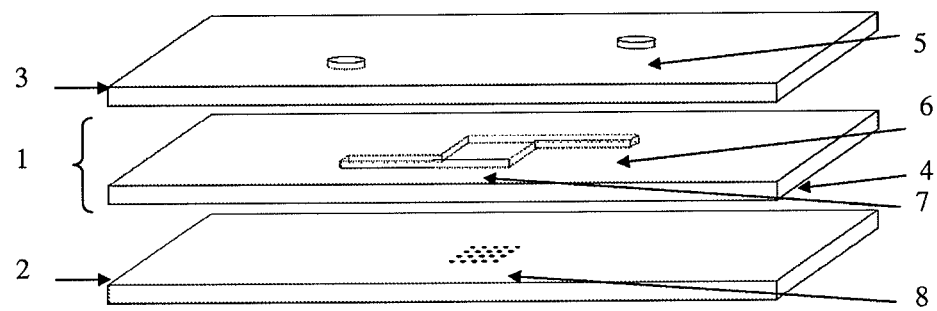
FIG. 2 is the schematic diagram showing the three-dimensional structure of the automatic sample loading device described in Example 2, wherein: 1 is the automatic sample loading device; 2 is the microarray chip; 3 is the cover plate; 4 is the microfluid layer; 5 is the through hole; 6 is the microfluid channel; 7 is the hybridization chamber; and 8 is the bio-probe array.

An Automatic Sample Loading Device and an Automatic Sample Loading Hybridization Microarray Chip Containing One Sample Loading Unit As shown in FIG. 2, the automatic sample loading device 1 containing one sample loading unit is formed by the hydrophilic cover layer 3 and the microfluid layer 4 through sealing, wherein after chemical modification, the lower surface of glass cover plate 3, i.e., the surface contacting the microfluid layer 4, has a static contact angle of 15 degrees with water, while the upper surface, after hydrophobic treatment, has a static contact angle of 1.00 degrees with water, and a through hole 5 is disposed on the cover layer 3 for the solution to pass through. The thickness of the microfluid layer 4 is about 0.2 mm, the substrate of the microfluid layer is polyethylene terephthalate (PET), with both lower and upper surface homogenously coated by acrylic adhesive, and a hollow microfluid channel 6 and hybridization chamber 7 are disposed on the microfluid layer 4; one end of the microfluid channel 6 is connected to the hybridization chamber 7, and the other end to the through hole 5 of the cover layer 3. An automatic sample loading device is formed through the sealing between the upper surface of the microfluid layer 4 and the lower surface of the cover plate 3 by acrylic adhesive. An automatic sample loading hybridization microarray chip is formed through sealing the lower surface of the microfluid layer 4 on said automatic sample loading device by the acrylic adhesive with the microarray chip 2, wherein the microarray chip 2 can be a glass based DNA chip or protein chip; the hybridization chamber 7 is connected to the bio-probe array 8 of the microarray chip 2, the shape and area of the hybridization chamber correspond to those of the bio-probe array of the microarray chip.

Example 3

The Automatic Sample Loading Device Containing a Plurality of Sample Loading Units FIG. 3(*b*) is the schematic diagram showing an automatic sample loading device containing 4 sample loading units. The material used for the cover plate is polymethylmethacrylate (PMMA), the lower surface of the cover plate has a static contact angle of 6 degrees with water after modified by polyvinyl alcohol (PVA), while the upper surface with no modification has a static contact angle of 78 degrees with water; the material for the microfluid layer is silicon wafer.

In contrast to Example 1 and 2, the size for the cover layer and the microfluid layer is large, so that 4 sample loading units are disposed side by side; the microfluid layer of the automatic sample loading device is sealed with 4 microarray chips by adhesive, to form a plate structure with microfluid channels inside, wherein the microfluid channels in each sample loading unit are not connected with each other, while a hybridization chamber is connected to the corresponding bio-probe array of the microarray chip, so that sample loading can be performed simultaneously to 4 microarray chips.

Example 4

Figure 4:
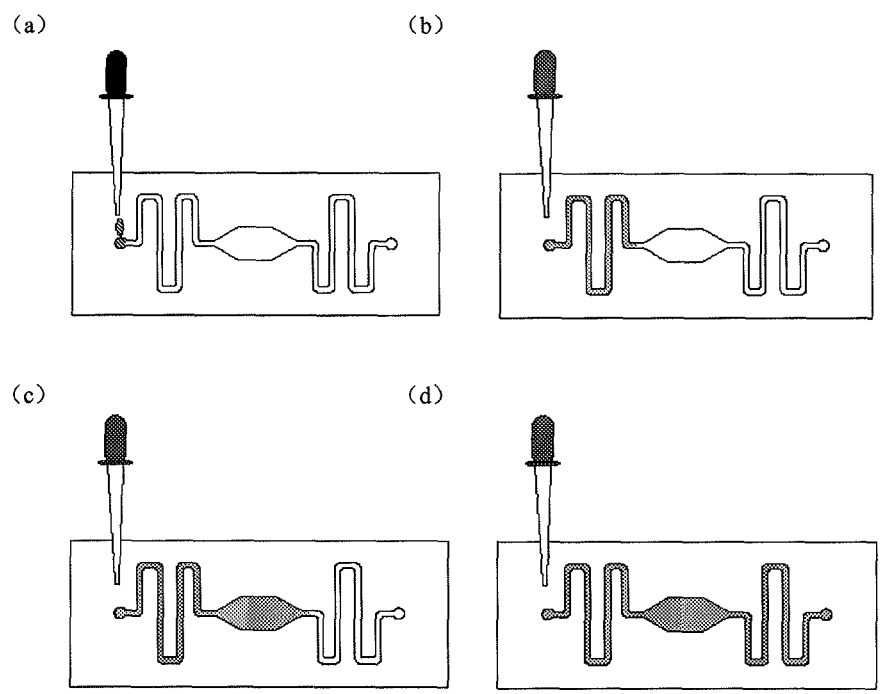
FIG. 4 is the schematic diagram showing the sample loading process of the automatic sample loading device described herein, wherein: (a) the sample solution arrives at the sample inlet when t=0; (h) the sample solution enters the microfluid channel automatically when t=3 s; (c) the sample solution enters the hybridization chamber automatically when t=6 s; (d) the sample solution fills the channel and the chamber completely when t=9 s, and the loading process is ended.

The Method for Using of the Automatic Sample Loading Hybridization Microarray Chip Described Herein First, about 60 µl DNA sample is loaded into the through hole using a pipette, and subsequently, the sample solution flows into the flow channel automatically, due to the super hydrophilic property of the surface of the cover plate, until the flow channel and the hybridization chamber are completely filled. As shown in FIG. 4, the sample solution arrives at the inlet when t=0 s; the sample solution enters the microfluid channel automatically when t=3 s; the sample solution enters the hybridization chamber automatically when t=6 s; the sample solution fills the channel and the chamber completely when t=9 s, and thereby the loading process is finished.

Figure 5:
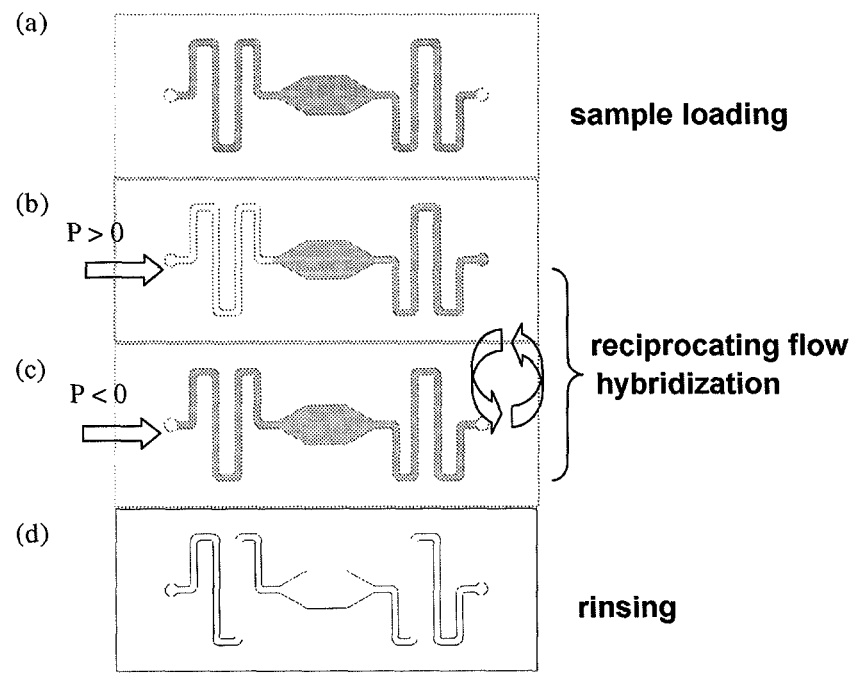
FIG. 5 is the schematic flow diagram showing the use of the automatic sample loading device, wherein: (a) original state; (b) movement of the fluid from left to right forced by positive pressure; (c) movement of the fluid from right to left forced by negative pressure and then back to the original position so that finishing one circulation of the reciprocating flow; (d) rinsing after hybridization.

At the beginning of hybridization, the pump valve for providing gas pressure is connected to the sample inlet. Subsequently, the sample solution is driven by positive pressure until the DNA sample arrives at the hybridization chamber; and the sample solution is then driven back under negative pressure until the DNA sample returns to the sample inlet under the negative pressure, as shown in FIG. 5. The positive pressure and negative pressure is alternatively repeated, in order to achieve reciprocating flow hybridization reaction. The whole process of hybridization takes less than 10 min. After the hybridization reaction, the sample solution is removed out of another through hole through the microfluid channel under positive pressure.

Figure 6:
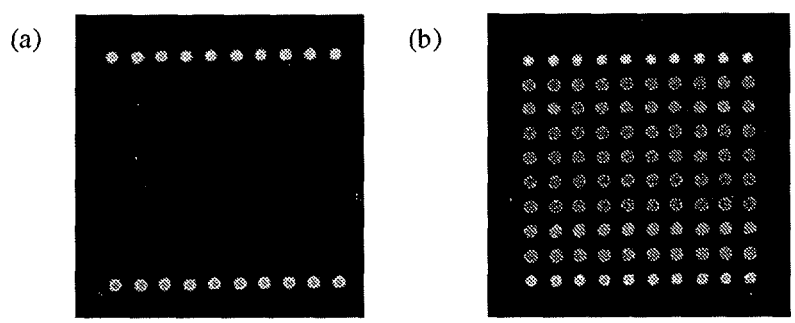
FIG. 6 is the fluorescent micrographs showing the microarray chip hybridization experiment using the automatic sample loading device described herein, (a) the fluorescent micrograph before hybridization; (b) the fluorescent micrograph after hybridization.

The hybridization chamber is rinsed by the rinsing solution loaded into the solution inlet by the pump valve. After dried, the chip is detected on a scanner. The result is shown in FIG. 6, suggesting that the hybridization signal of high intensity (signal-to-noise ratio higher than 100) can be obtained with 60 µL hybridization sample in 10 min.

The content described above is only the preferable embodiments of the present invention, and it should be noted that several improvements and modifications can be made by the person of ordinary skill in the art without departing from the principles of the present invention. These improvements and modifications should also be regarded as in the scope of the present invention.

The automatic sample loading device for microarray chip and the method for using said device provided herein have been described by Examples, and it is apparent that modification or proper change and combination can be made to the automatic sample loading device for microarray chip and the method for using said device described herein by those skilled in the art, without departing from the content, spirit and scope of the invention, in order to achieve the techniques disclosed in the present invention. In particular, it should be pointed out that all similar substitutions and modifications become apparent to those skilled in the art, and they are deemed to be within the spirit, scope and content of the present invention.

The invention claimed is:

1. An automatic sample loading device for microarray chip, characterized in that the automatic sample loading device comprises at least one sample loading unit, said sample loading unit is formed by sealing a cover layer with a hydrophilic surface to a microfluid layer, the cover layer is configured with at least two through holes, and the microfluid layer is configured with a hollow hybridization chamber and at least two hollow microfluid channels, wherein one end of each of the microfluid channels is connected to the hybridization chamber, and the other end is connected to one of the through holes of the cover layer, wherein the contact angle between the surface of the cover layer which contacts the microfluid layer and a sample solution is less than 90 degrees when the sample solution is water, and wherein the contact angle between the other surface of the cover layer and a sample solution is in the range of 90 to 180 degree when the sample solution is water.

2. The automatic sample loading device according to claim 1, characterized in that the material for the cover layer is selected from the group consisting of glass, polymers, silicon wafer, metals and metal oxides.

3. The automatic sample loading device according to claim 1, characterized in that the material for the microfluid layer is selected from the group consisting of glass, polymers, silicon wafer, metals and metal oxides.

4. The automatic sample loading device according to claim 1, characterized in that the microfluid layer includes substrate layer, upper adhesive layer and lower adhesive layer.

5. The automatic sample loading device according to claim 4, characterized in that the material for the substrate layer is selected from the group consisting of glass, polymers, silicon wafer, metals and metal oxides, and the adhesive for the upper adhesive layer and the lower adhesive layer is selected from the group consisting of calendering adhesive, melt adhesive, reactive adhesive, solvent adhesive, emulsion adhesive and solventless liquid adhesive.

6. The automatic sample loading device according to claim 1, characterized in that the hollow hybridization chamber and two microfluid channels of the microfluid layer are formed by laser ablation, machining or chemical etching.

7. The automatic sample loading device according to claim 1, characterized in that the shape and area of the hybridization chamber corresponds to those of a bio-probe array of the microarray chip.

8. An automatic sample loading hybridization system comprising the automatic sample loading device of claim 1 and a microarray chip, wherein the microfluid layer of the automatic sample loading device is sealed with the microarray chip, and the hybridization chamber is connected to a bio-probe array of the microarray chip.

9. The automatic sample loading hybridization system according to claim 8, wherein the microarray chip is selected from the group consisting of RNA chip, cDNA chip, PNA chip, protein chip and carbohydrate chip.

10. A method for using the automatic sample loading device of claim 1, the method comprising:

Step 1: sealing the microfluid layer of the automatic sample loading device with a microarray chip, wherein the sealing results in the connection between the hybridization chamber of the microfluid layer and a bio-probe array of the microarray chip;

Step 2: loading a sample solution at one through hole of a sample loading unit of the automatic sample loading device, wherein the sample solution enters and fills the microfluid channel connected with said through hole;

Step 3: connecting said through hole to a pump valve which provides a gas pressure, wherein the gas pressure serves as the driving force for a reciprocating flow of the sample solution in the hybridization chamber and the two microfluid channels.

11. The method according to claim 10, wherein the reciprocating frequency of the reciprocating flow is in the range from 0 to 100 Hz.

12. The method according to claim 10, wherein the gas pressure is in the range from 0 to 1 MPa.

13. The method according to claim 10, further comprising a step of removing the sample solution from another through hole of the sample loading unit with the gas pressure as the driving force.

14. The method according to claim 10, wherein the microarray chip is selected from the group consisting of RNA chip, cDNA chip, PNA chip, protein chip and carbohydrate chip.

* * * * *